United States Patent
Holmes et al.

(10) Patent No.: US 6,411,106 B1
(45) Date of Patent: Jun. 25, 2002

(54) METHOD AND APPARATUS FOR MOISTURE SENSING USING MICROWAVE TECHNOLOGIES

(75) Inventors: Wayne S. Holmes, Wainku; Stephen G. Riley, Rotorua; Richard B. Keam, Auckland, all of (NZ)

(73) Assignee: Industrial Research Limited, Parnell (NL)

( * ) Notice: Subject to any disclaimer, the term of this patent is extended or adjusted under 35 U.S.C. 154(b) by 0 days.

(21) Appl. No.: 09/684,171

(22) Filed: Oct. 5, 2000

Related U.S. Application Data

(63) Continuation-in-part of application No. 09/087,262, filed on May 29, 1998, now abandoned, which is a continuation of application No. PCT/NZ98/00134, filed on Nov. 29, 1996.

(30) Foreign Application Priority Data

Nov. 29, 1995 (NZ) ................................. 280557

(51) Int. Cl.[7] ............................................... G01R 27/04
(52) U.S. Cl. ........................ 324/643; 324/642; 324/645
(58) Field of Search .................................. 324/643, 640, 324/639, 642, 645, 629

(56) References Cited

U.S. PATENT DOCUMENTS

| | | | | |
|---|---|---|---|---|
| 3,551,806 A | * | 12/1970 | Sasaki | 324/640 |
| 5,103,181 A | * | 4/1992 | Gaisford et al. | 324/637 |
| 5,331,284 A | * | 7/1994 | Jean et al. | 324/639 |

FOREIGN PATENT DOCUMENTS

| | | |
|---|---|---|
| SU | 1196742 A | 12/1985 |
| SU | 1285362 A | 1/1987 |

\* cited by examiner

*Primary Examiner*—Diego Gutierrez
*Assistant Examiner*—Anjan K Deb
(74) *Attorney, Agent, or Firm*—Sheldon & Mak; Robert J. Ross

(57) ABSTRACT

This invention provides a method and apparatus for the sensing of moisture using microwave technology. The apparatus provides a wave guide having a linear array of slots in its broadwall. A detector detects reflected energy of microwave signals over a frequency range once the material is positioned over the slots. A value indicative of the power spectral density of the reflected signals is computed and a value for the moisture content of the material determined from the value of power spectral density. The slots are at an angle with respect to the longitudinal axis of the wave guide and the angle can be varied according to the material being tested.

12 Claims, 3 Drawing Sheets

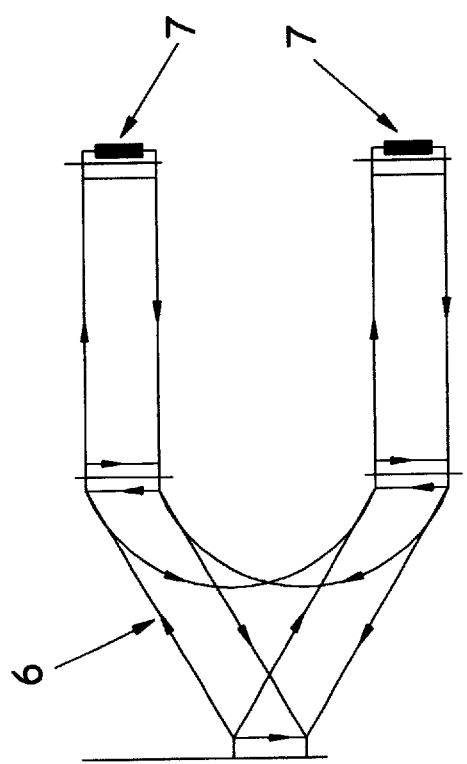
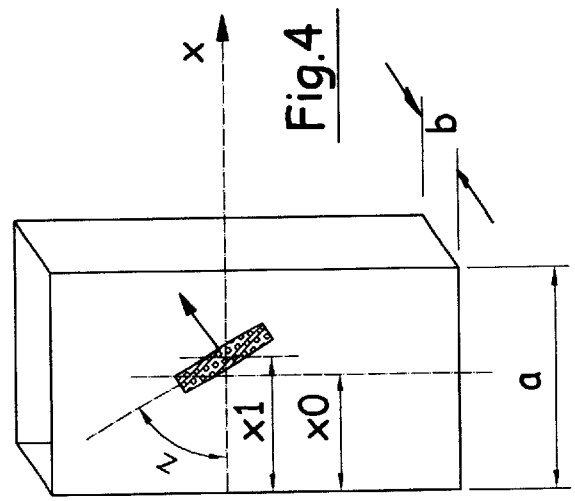
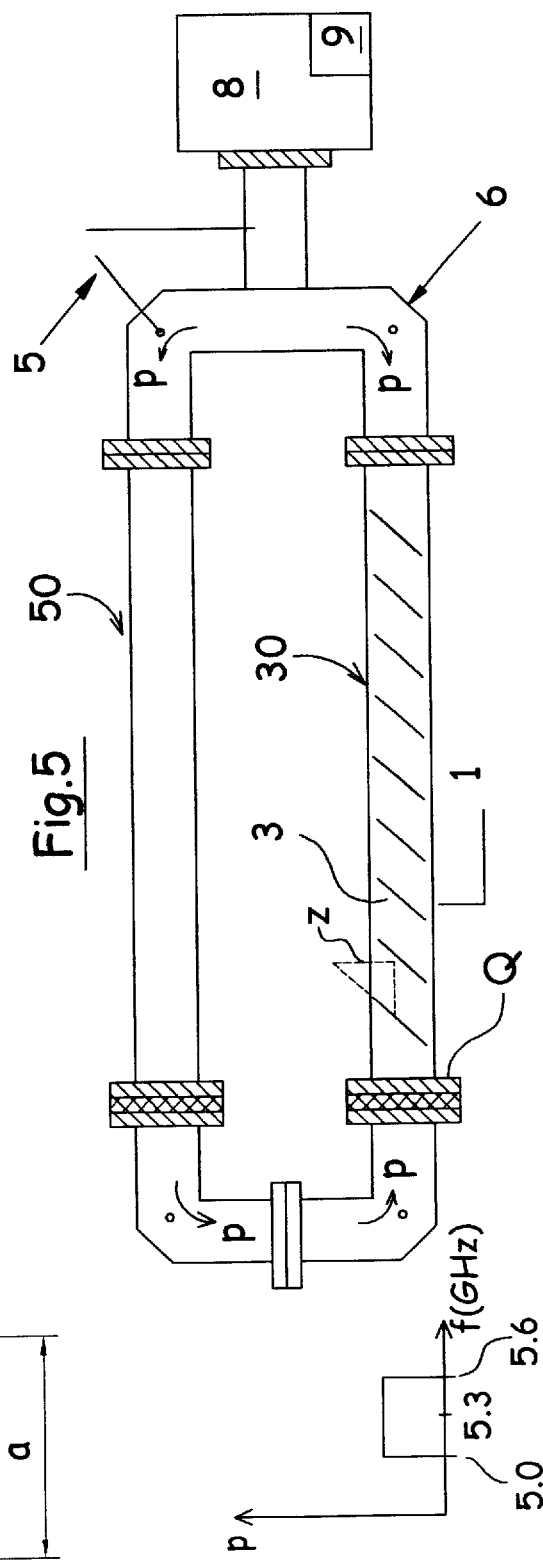

METHOD AND APPARATUS FOR MOISTURE SENSING USING MICROWAVE TECHNOLOGIES

CROSS REFERENCE TO RELATED APPLICATIONS

This application is a continuation-in-part of application Ser. No. 09/087,262 filed May 29, 1998, now abandoned, which was a continuation of PCT Application PCT/NZ98/00134, entitled METHOD AND APPARATUS FOR MOISTURE SENSING USING MICROWAVE TECHNOLOGIES and filed Nov. 29, 1996, which takes priority from New Zealand Patent Application No. 280557 filed Nov. 29, 1995, the contents of each of which are incorporated herein in their entirety.

BACKGROUND

The present invention relates to improvements in and relating to methods and apparatus for the sensing of moisture using microwave technologies.

More particularly but not exclusively the present invention relates to the sensing of moisture in timber. However as will be appreciated by those skilled in the engineering and electrical arts the present invention could find application wherever moisture of a non-metallic and particularly an organic material was required. It is envisioned for example that the present invention could find application in the moisture sensing of organic material such as wool or other fibrous materials.

For simplicity, the present invention will be described in respect to its use in the moisture sensing for timber.

Timber in New Zealand and many other countries is dried artificially in kilns. It is important that the dryness of the timber be monitored in situ so that the drying can be terminated at the appropriate level. Current techniques based solely on time typically result in timber being overdried necessitating its subsequent reconditioning. This of course means that time and money is wasted in excessive drying and in the reconditioning.

To alleviate these problems various types of in situ sensors have been proposed. As they are required to be installed within a kiln operating at possibly 180° C.–200° C. such sensors need to be robust and readily calibrated. Some previous probes have relied on the measurements of capacitance or resistance as an indicator of moisture level. Such probes have been found to be fragile, inaccurate and/or difficult to calibrate.

OBJECT OF THE INVENTION

It is an object of the present invention to provide methods and/or apparatuses for the sensing of moisture level in a material using microwave technologies and to overcome or at least obviate the disadvantage of prior art apparatuses/methods.

Further objects of the present invention may become apparent from the following description.

SUMMARY OF THE INVENTION

According to one aspect of the present invention there is provided an apparatus for sensing the moisture content of a material, the apparatus including a wave guide having a linear array of slots in its broadwall, a generator to generate microwave signals over a predetermined frequency range for transmission along the waveguide, a detector suitable for detecting the energy of reflected microwave signals from the waveguide with the material positioned over the slots, a processor to compute a value indicative of the power spectral density of the reflected microwave signals over the predetermined frequency range, wherein the moisture content of the material is determined according to a predetermined relationship between the computed value indicative of the power spectral density and moisture content of the material.

According to another aspect of the present invention, there is provided a method of sensing the moisture of a material, the method including the steps of:

(a) positioning the material over a linear array of slots located in the broadwall of a wave guide;

(b) transmitting one or more microwave signals covering a predetermined frequency range along the waveguide;

(d) detecting the energy reflected from the waveguide of each microwave signal;

(e) computing a value indicative of the spectral density of the reflected microwave signals over the predetermined frequency range; and (f) determining the moisture content of the material by matching the computed value with a predetermined value of moisture content.

According to a further aspect of the present invention there is provided a moisture sensing arrangement and/or a method of moisture sensing substantially as herein described and/or with reference to the accompanying drawings.

Further aspects of this invention which should be considered in all its novel aspects may become apparent from the following description.

BRIEF DESCRIPTION OF THE DRAWINGS

The description is given by way of example of possible embodiments thereof and in which reference is made to the accompanying drawings wherein:

FIG. 4: Shows very diagrammatically wave guide and slot dimensions;

FIG. 5: Shows very diagrammatically a wave guide according to one possible embodiment of the invention;

FIG. 6: Shows very diagrammatically a signal flow representation of an array feed structure for the wave guide of FIG. 5;

DETAILED DESCRIPTION OF PREFERRED EMBODIMENTS

As will be appreciated by those involved in production, manufacture or construction industries involving timber products, a knowledge of the moisture content of timber can be critical in order to minimize costs involved in the processing or even downgrading of incorrectly dried material. Moisture content is also a critical factor in minimizing stress and in avoiding brownstaining of timber.

The present invention has been developed particularly in response to the need for identifying the required moisture content of soft woods such as Radiata Pine which are able to be dried very quickly at elevated temperatures. However, the present invention has application in moisture sensing for all types of timber and as mentioned previously for other electrically non-conductive materials, especially organic materials such as wool and the like.

Typically, in the drying of timber at least in New Zealand, it will be dried in batches with stack widths up to 2.4 m wide. With a typical lateral flow of air through the kiln a variable drying effect can result so it is important to be able to accurately assess an average moisture content across a stack with the sensing means being sufficiently robust as to be able to cope with drying temperatures of up to 200° C. and to be sufficiently cheap so as to enable a plurality of sensing means to be provided for any particular kiln.

The present invention utilizes microwave technologies to achieve a required moisture sensing, particularly of timber being dried in a kiln.

Figure 1:
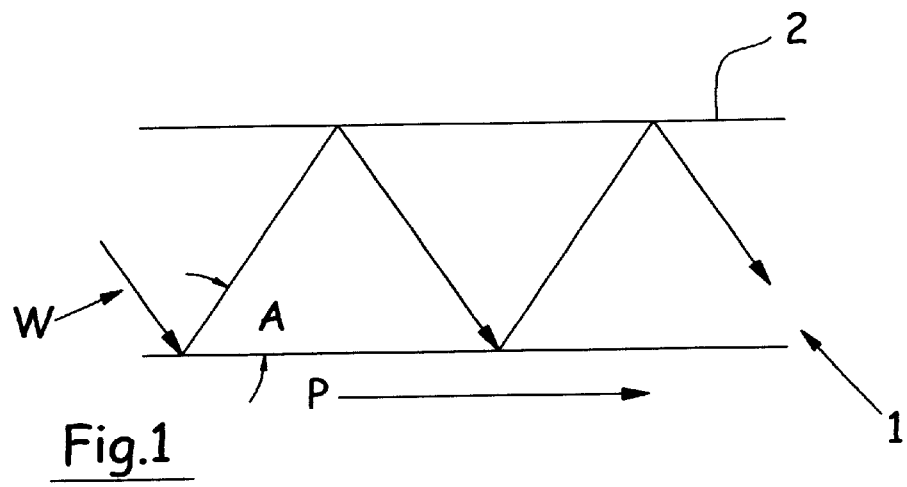
FIG. 1: Shows very diagrammatically the wave propagation in a rectangular wave guide.

Referring to FIG. 1 a rectangular wave guide is referenced generally by arrow 1 and shows a wave front W traveling along the wave guide 1, with the direction of power flow indicated by arrow P. The wave front W is shown diagrammatically as being reflected off the wave guide walls 2 with the distance between its intersections with the walls 2 being a function of the wave length and the angle of reflection A.

Figure 2:
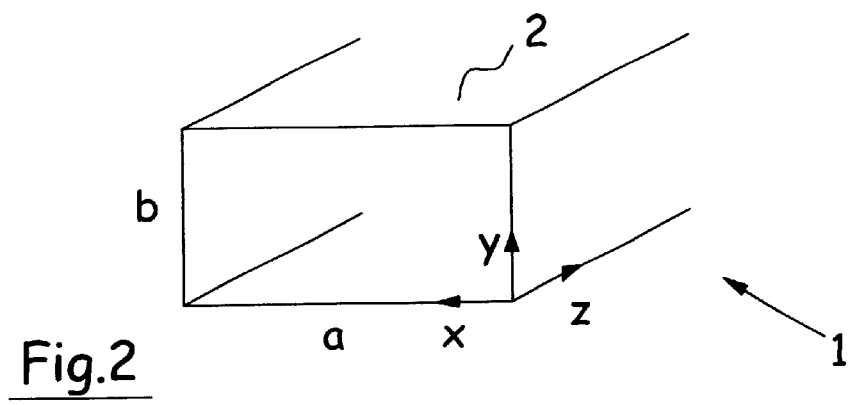
FIG. 2: Illustrates dimensions within a rectangular wave guide.

The electric field (E) utilized in the present application may be that known as the $TE_{10}$ mode which can be expressed as:

$$E_x = E_o \sin\left(\frac{\pi x}{a}\right)$$

where the E field is a constant value in the y direction and varies in a half sine wave in the x direction as shown in FIG. 2.

In using microwave technology in the present invention the interaction between the material for which the moisture content is to be sensed and the microwave electric field is provided by providing a slot array in the broadwall of the wave guide 1.

Figure 3:
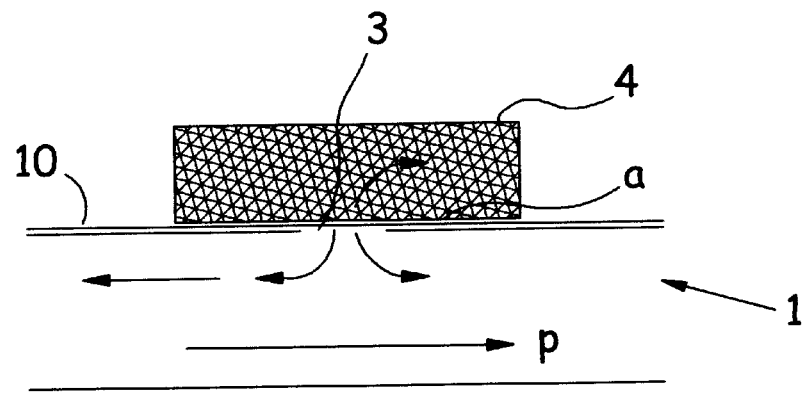
FIG. 3: Shows very diagrammatically incident, radiated and reflected wave travel through a wave guide slot.

In FIG. 3 a single slot of a slot array 30 is referenced generally by arrow 3 and as illustrated very diagrammatically, the microwave energy propagated in the direction P when incident at a resonant length aperture in the broadwall, a, will partially radiate from the slot 3 and will partially be reflected back into the wave guide 1. The ratio of the reflected energy to the transmitted energy is governed by the permittivity of the material 4 which can, for example, be a stack of timber. It has been established that the permittivity of a material such as timber is directly related to the moisture content so that detection of the permittivity value can enable the corresponding detection of the moisture content.

In providing an array of slots 3 in the broadwall, a, of the wave guide 1, the positioning, angle and width of the slots 3 will influence the radiation characteristics of the slot 3 as will the excitation voltages established by the propagating modes within the wave guide 1 and the characteristics of the materials both inside and outside the wave guide 1.

Where:
p=reflection coefficient (quantitative ratio of reflected electric field to the incident electric field)
k=free space wave number
B=phase constant in the wave guide
a=broadwall dimension
b=side wall dimension
Z=angle of slot with respect to the longitudinal axis of the wave guide, then $$p = \frac{73\pi k B a b}{60|(F(Z))|}$$

where:

$$F(Z) = \frac{j\pi}{k}\left[B\sin(ZI(Z)) + \frac{\pi}{a}\cos(ZJ(Z))\right]$$

In one embodiment the slot 3 can be chosen to be a resonant length in air at 5.3 GHz and to be excited by the dominant $TE_{10}$ mode in the wave guide. With the slot 3 centred in the broadwall, a, a slot angle Z of typically 78° was utilised for a timber material, a slot in this configuration being analogous to a serious of lumped admittances at intervals along the wave guide 1.

Depending on the material being measured the appropriate slot angle may vary between 45° to 90° for example.

In one embodiment an array of slots 3 may be driven from a single end with the other end terminated in a lossy load to absorb the microwave energy which was not absorbed or reflected by the covering wood or other material. Such an array structure is commonly termed a travelling wave array.

However, for improved sensitivity in averaging moisture content across the material it is considered preferable to utilise a standing wave aperture array in which each slot 3 is now driven from travelling waves incident from both ends of the array. This has the effect of setting up a standing wave inside the wave guide 1 exciting the slots 3 which at certain frequencies forces all the slots 3 to be in phase. The establishment of the standing wave may be by means of an electrical short circuit reflecting the incident wave back down the array or by directly exciting the array from both ends.

An embodiment of the invention utilizing the latter technique is indicated very diagrammatically in FIG. 5 by arrow 50.

In FIG. 5 the wave guide 1 has an array of slots 3 which is driven at both ends with equal amounts of power by utilizing a splitter. The phase of the incident E fields at either end of the array 30 is equal so that the peaks of the standing wave at the desired frequency drive the slots 3 with the same excitation. As shown in FIG. 5 the splitting and combining function may be provided by an H-plane splitter 6 which has the effect of producing two transmission lines in parallel offering a matched load of half the characteristic impedance of the wave guide 1 at the measurement plane. The splitter 6 may be tuned using reactive obstacles in the wave guide 1 and suitably by providing a tuning screw 5 between the measurement plane and the splitter 6.

As indicated in FIG. 6 the admittance 7 offered by the slot array does not significantly affect the wave guide feeding structure so that tuning of the feed section will not greatly affect the sensitivity of the slot array 30. Following matching of the slot array 30 to the measurement system, the phase of the incident microwave energy at each end can be adjusted by means of electrical length adjustments of the feeder to port Q using a tuning screw in the output of the splitter 6. Such an adjustment is necessary so that the standing wave created inside the array, forces each slot 3 to be at a field maxima.

The wave guide 1 will thus be inserted into the kiln so as to be above or below the timber being dried and with the slots 3 facing the timber. The coupling of the wave guide 1 externally of the kiln may preferably be thermally isolated and this may be achieved for example by a means of providing the wave guide coupling with a water jacket or possibly by using coaxial cable.

It is also mentioned that a problem can arise in the condensation of water within the wave guide 1. It may therefore be appropriate to include a microwave transparent material 10 (see FIG. 3) such as a plastics so as to cover over the slots 3 and to prevent moisture ingress, or as a plastic barrier inside the waveguide to prevent moisture egress from the kiln.

As previously mentioned, a measure of the microwave reflection coefficient needs to be determined in order to provide a measurement of the permittivity and therefore a measurement of moisture content. For this purpose a vector network analyser 8, such as a Hewlett Packard 8720B can be configured to detect reflected energy from the waveguide at each frequency through a required frequency range which in one embodiment of the invention could for example be 5.0–5.6 GHz. The frequency range is centred around the resonant frequency of 5.3 GHz (see FIG. 5) and allows a number of measurements to be taken at varying frequencies in order to reduce the effects of noise.

Using a standard microwave "Through, Reflect, Line" algorithm, this places the measurement reference plane at the wave guide transition flange so that the measurement of the reflected energy and thus the reflection coefficients effectively takes place within the wave guide structure and reflections due to the input coaxial and a waveguide to coaxial cable transitions are removed.

Suitably a software program can control the vector network analyser remotely and allows for measurements to be taken and stored at predetermined intervals during the drying period. The length of any interval can be selected depending on the anticipated length of the drying period.

In determining the average moisture content from the measurements taken the following manipulation can be performed:

(i) the magnitude of the reflected energy is detected for all the frequency points measured throughout the predetermined frequency range;

(ii) the magnitude of the reflected energy detected at each frequency covering the required range, for example 5.0–5.6 GHz is summed producing a measure indicative of the power spectral density, having the effect of reducing measurement noise;

(iii) the process is repeated for all measurements in the drying run.

It will be appreciated by those skilled in the art that the more measurements that are taken over the frequency range, the closer the sum of the individual energy measurements will come to the actual power spectral density over the frequency range, to the limit of ramping the frequency and integrating the response. The number of measurements taken may depend on limitations in processing power, the maximum delay before a result is required and the minimum step size of the microwave generating equipment.

Figure 8:
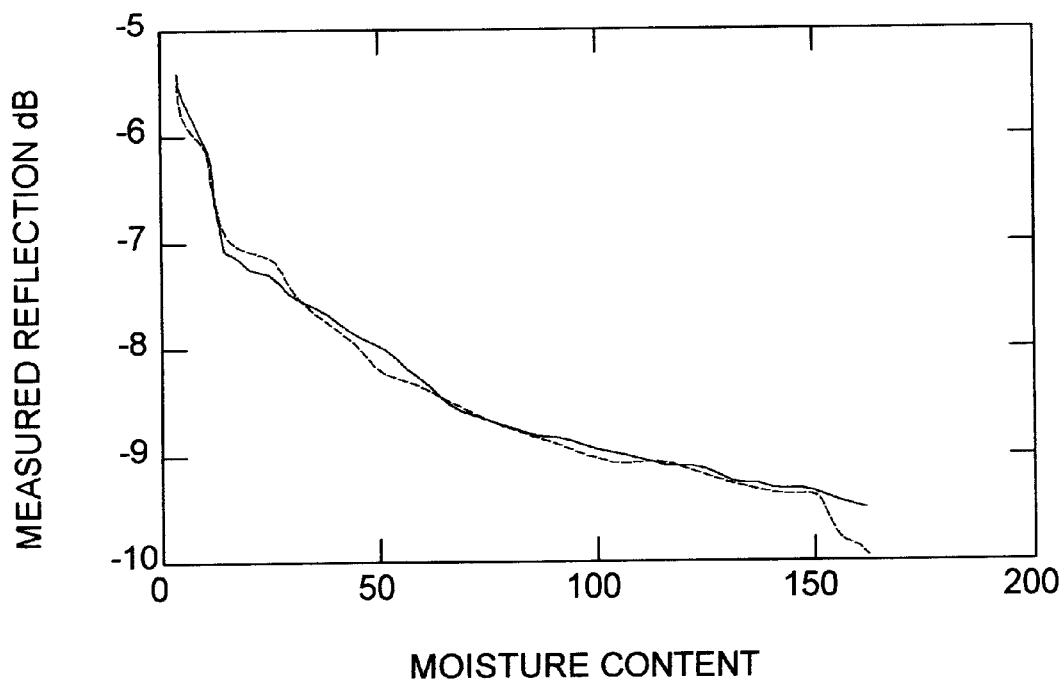
FIG. 8: Shows a plot of measured reflected microwave signals against moisture content for a particular stack of timber.

FIG. 8 shows a plot of the measure of power spectral density as a function of the average moisture content for a particular charge of timber.

Figure 7:
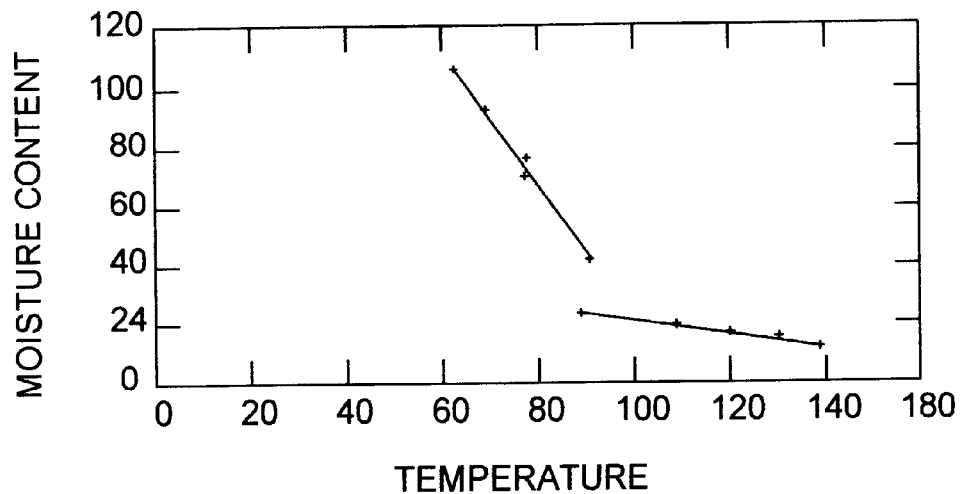
FIG. 7: Provides a plot of moisture content against temperature for a particular batch of timber.

It has been found that there are three distinct regions in which approximately linear response of the microwave measurements to moisture content is obtained, each with a different gradient. It is believed that the first region at high moisture content is controlled by mass liquid flow as the major factor in the drying process and, after the free water is removed, vapour movement is believed to dominate and with the final region being at the dry end of the drying process, around 10% moisture content. The value of the moisture content at which these regions intersect can be readily determined as shown in FIG. 7 where the relatively steeply sloped graph for the high moisture content intersects as a "knee" with the lesser slope of the lower moisture content.

The prediction of the "knees" can be readily determined so that moisture content can be then readily related back to the microwave measurements of the reflection coefficient.

It is seen therefore that the present invention can provide a speedy and effective measurement of moisture content in a material utilizing microwave technologies and which can be performed in difficult environments such as those present in a timber drying kiln.

Where in the foregoing description reference has been made to specific components or integers of the invention having known equivalents then such equivalents are herein incorporated as if individually set forth.

Although this invention has been described by way of example and with reference to possible embodiments thereof it is to be understood that modifications or improvements may be made thereto without departing from the scope of the invention as defined in the appended claims.

What is claimed is:

1. An apparatus for sensing the moisture content of a material, the apparatus including a wave guide having a linear array of slots in its broadwall, a generator to generate microwave signals over a predetermined frequency range for transmission along the waveguide, a detector suitable for detecting the energy of reflected microwave signals from the waveguide with the material positioned over the slots, a processor to compute a value indicative of the power spectral density of the reflected microwave signals over the predetermined frequency range, wherein the moisture content of the material is determined according to a predetermined relationship between the computed value indicative of the power spectral density and moisture content of the material.

2. The apparatus according to claim 1, wherein the slots are at a predetermined angle with respect to the longitudinal axis of the wave guide and the angle is determined dependent on the material being sensed.

3. The apparatus according to claim 2, wherein the slots include a standing wave aperture-array.

4. The apparatus according to claim 3, wherein the generator is adapted to generate a standing wave within the waveguide, wherein each slot is substantially commensurate with a maxima of the standing wave and wherein the distribution of frequency of the generated signals is substantially centred around the standing wave frequency.

5. The apparatus according to claim 4, wherein the slots include a microwave transparent moisture resistant covering.

6. The apparatus according to claim 5 including an H-plane splitter to feed the slot array from both ends.

7. A method of sensing the moisture of a material, the method including the steps of:

(a) positioning the material over a linear array of slots located in the broadwall of a wave guide;

(b) transmitting one or more microwave signals covering a predetermined frequency range along the waveguide;

(d) detecting the energy reflected from the waveguide of the or each microwave signal;

(e) computing a value indicative of the spectral density of the reflected microwave signals over the predetermined frequency range; and (f) determining the moisture content of the material by matching the computed value with a predetermined value of moisture content.

8. The method of moisture sensing as claimed in claim 7, wherein the slots provided in step (a) are at an angle with respect to the longitudinal axis of the wave guide, wherein the angle is dependent on the material being sensed.

9. A method of moisture sensing as claimed in claim 8, wherein the method includes transmitting a standing wave along the waveguide, wherein each slot is substantially commensurate with a maxima of the standing wave and wherein the distribution of frequency of the generated signals is substantially centred around the standing wave frequency.

10. A method of moisture sensing as claimed in claim 9, wherein the slots include a microwave transparent, moisture resistant covering.

11. A method of moisture sensing as claimed in claim 10, wherein the wave guide provided includes an H-plane splitter such that the slot array is fed from both ends.

12. A method of moisture sensing as claimed in claim 8, wherein the slots provide a standing wave aperture array.

* * * * *

UNITED STATES PATENT AND TRADEMARK OFFICE
CERTIFICATE OF CORRECTION

PATENT NO. : 6,411,106 B1
DATED : June 25, 2002
INVENTOR(S) : Holmes et al.

It is certified that error appears in the above-identified patent and that said Letters Patent is hereby corrected as shown below:

<u>Title page,</u>
Item [75], delete "Wainku" and substitute -- Waiuku --.
Item [73], delete "NL" and substitute -- NZ --.
Item [74], delete "Ross" and substitute -- Rose --.

Signed and Sealed this

Fourteenth Day of January, 2003

JAMES E. ROGAN
*Director of the United States Patent and Trademark Office*